United States Patent [19]

Broersma, Jr. et al.

[11] 4,343,810
[45] Aug. 10, 1982

[54] METHOD OF INHIBITING SICKLING OF SICKLE ERYTHROCYTES USING 2-((HALOANILINO)METHYL)-2-IMIDAZOLINES

[75] Inventors: Robert J. Broersma, Jr., Noblesville, Ind.; Gayle A. Spittka, Midland, Mich.

[73] Assignee: The Dow Chemical Company, Midland, Mich.

[21] Appl. No.: 200,248

[22] Filed: Oct. 24, 1980

[51] Int. Cl.³ .......................................... A61K 31/415
[52] U.S. Cl. .............................................. 424/273 R
[58] Field of Search ................................... 424/273 R

[56] References Cited

PUBLICATIONS

Raper–"Ann. Soc. Belge Med. Trop.", 1969, 49, 2, 205–210.

*Primary Examiner*—Frederick E. Waddell

[57] ABSTRACT

Method for inhibiting the sickling of sickle erythrocytes in blood by contacting the sickle erythrocytes with a compound of the formula:

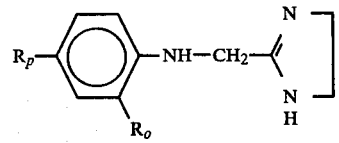

or a pharmaceutically-acceptable salt thereof, wherein $R_o$ represents chloro, bromo, fluoro or iodo; and $R_p$ represents hydrogen, chloro, bromo, fluoro or iodo.

3 Claims, No Drawings

METHOD OF INHIBITING SICKLING OF SICKLE ERYTHROCYTES USING 2-((HALOANILINO)METHYL)-2-IMIDAZOLINES

BACKGROUND OF THE INVENTION

In the adult human most hemoglobin is hemoglobin A (Hb-A) consisting of two alpha and two beta polypeptide chains. Certain individuals have an abnormal hemoglobin known as hemoglobin S (Hb-S) which results from the hereditary substitution of valine for glutamic acid in the sixth amino acid position in the beta polypeptide chains of hemoglobin. The proportion of Hb-S to Hb-A in such an individual depends upon whether the individual is a homozygous or heterozygous individual. The tendency toward sickling, that is, the formation of abnormally shaped erythrocytes in which the erythrocytes assume a sickle shape, depends upon the amount of Hb-S in the erythrocyte and the level of oxygen tension. Erythrocytes with 100 percent Hb-S sickle at physiological oxygen tensions, however as the amount of Hb-A increases and Hb-S decreases progressively lower oxygen tensions are required to induce sickling. The homozygous individual has 80 to 100 percent of the hemoglobin in the Hb-S form and sickling occurs at ordinary oxygen tensions. Such individuals are said to have sickle cell disease. Heterozygous individuals are said to possess sickle cell trait since only 25 to 40 percent of their hemoglobin is Hb-S, and sickling occurs only at unusually low oxygen tensions.

The presence of sickled erythrocytes can have severe implications since sickled erythrocytes encounter mechanical difficulties in moving through small vessels and the consequent stasis and jamming of these cells can lead to thrombosis and tissue anoxia. In addition, because of the sickled erythrocytes' increased mechanical fragility, hemolysis results. S. L. Robbins and M. Angell, "Basic Pathology", W. B. Saunders Company, Philadelphia, London, Toronto, 1971, pp. 127 and 282.

A treatment or test in which the sickling of red blood cells prone to sickle (sickle erythrocytes) is inhibited or reversed would be useful in the treatment of afflicted individuals or for the study of the sickling phenomenon.

SUMMARY OF THE INVENTION

It has now been discovered that the sickling in blood of red blood cells prone to sickle can be inhibited by contacting the sickle erythrocytes in blood with an effective amount of a compound of the formula:

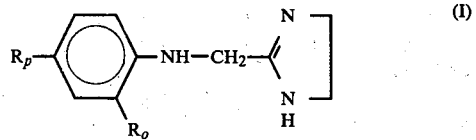

(I)

or a pharmaceutically-acceptable salt thereof, wherein $R_o$ represents chloro, bromo, fluoro or iodo; and $R_p$ represents hydrogen, chloro, bromo, fluoro or iodo.

"Pharmaceutically-acceptable salt" refers to non-toxic acid addition salts of the compounds, the anions of which are relatively innocuous to mammals at exposure levels or dosages consistent with activity or use of the compounds, so that the beneficial effects of the free base are not vitiated by the side effects, or mammalian toxicity, ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids.

As used herein, an effective amount of the compound represented by formula I or a pharmaceutically-acceptable salt thereof is that amount of the compound or its pharmaceutically-acceptable salt which when employed according to the method of the present invention is sufficient to inhibit the sickling of sickle erythrocytes in blood. As used in the specification and claims, "inhibiting" means inhibiting the formation of sickle morphology and also includes actively reversing sickled cells to a more normal or typical morphology, in cases in which sickling has already occurred. The compounds used in the practice of the present invention are therefore particularly useful in the study of the sickling phenomenon, in the investigation of the effects of chemical substances on erythrocytes and has potential usefulness as a treatment for individuals subject to the sickling phenomenon.

DETAILED DESCRIPTION OF THE INVENTION

The compounds used in the practice of the present invention, i.e., the compounds of formula I or a pharmaceutically-acceptable salt thereof, are prepared by reacting a substituted-anilinoacetonitrile represented by the formula:

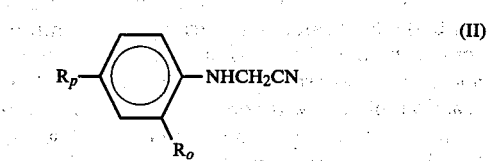

(II)

wherein $R_o$ and $R_p$ are defined as for formula I, with ethylenediamine p-toluenesulfonate. The reaction is conveniently accomplished employing a procedure similar to that used for the preparation of 2-((halophenoxy)methyl)-2-imidazolines, as described in U.S. Pat. No. 3,449,356. In preparing the 2-imidazoline compounds of formula I, the appropriate substituted-anilinoacetonitrile and the ethylenediamine p-toluenesulfonate are mixed and heated together in an inert organic solvent, such as 1,2-dichlorobenzene for a time sufficient to obtain the 2-((halo- or dihaloanilino)methyl)-2-imidazoline p-toluenesulfonate salt. The reaction is preferably carried out under an inert atmosphere, accomplished by passing nitrogen through the reaction mixture to carry off the ammonia formed during the reaction. The p-toluenesulfonate salt can be separated from the reaction mixture using known procedures such as the adjustment of reaction mixture concentration, filtration, centrifugation and decantation. Purification of the p-toluenesulfonate salt can be accomplished by conventional procedures such as recrystallization and washing.

Alternatively, the 2-((halo- or dihalo-anilino)methyl)-2-imidazoline p-toluenesulfonate salt can be converted to the free base form (i.e., free imidazoline) by hydrolysis in aqueous base. The free base is then separated by extraction with an organic solvent such as methylene chloride ($CH_2Cl_2$) or chloroform ($CHCl_3$), followed by evaporation of the solvent. Purification of the free base is accomplished by conventional methods such as recrystallization or the free base can be converted to a pharmaceutically-acceptable salt by treating the free base with the appropriate organic or mineral acid. The pharmaceutically-acceptable salt can be purified by known procedures such as recrystallization.

The substituted-anilinoacetonitrile, illustrated by formula II, is prepared by known procedures, for example, by heating a mixture of a substituted-aniline of the formula:

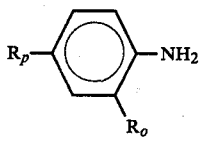

(III)

wherein $R_o$ and $R_p$ are as defined for formula I, and chloroacetonitrile for a time sufficient to obtain the desired acetonitrile. The acetonitrile is recovered and purified by conventional procedures such as those described herein.

The following examples are included to further illustrate the invention but are not to be construed as a limitation thereon.

EXAMPLE 1

2-((2,4-Dichloroanilino)methyl)-2-imidazoline (a) Preparation of 2,4-dichloroanilinoacetonitrile Chloroacetonitrile (40 ml) and 2,4-dichloroaniline (81.0 g) were heated with stirring in a 250 ml round-bottomed three-necked flask at 120°–125° C. for 1.0 hour and then for approximately 1 hour at 140°–145° C. The reaction mixture was cooled, diluted with $CH_2Cl_2$, and then placed in a separatory funnel and water added. Shaking the mixture resulted in crystal formation. The mixture was filtered and 39.2 g of 2,4-dichloroaniline hydrochloride removed. The $CH_2Cl_2$ layer was then separated from the filtrate and the $CH_2Cl_2$ layer treated with diatomaceous earth and activated charcoal and then filtered. The $CH_2Cl_2$ was then evaporated off, leaving a black viscous gum which on cooling with stirring solidified. Recrystallization from carbon tetrachloride gave 21.5 g of 2,4-dichloroanilinoacetonitrile.

(b) Preparation of 2-((2,4-dichloroanilino)methyl)-2-imidazoline

A mixture of 21.5 grams (g) of 2,4-dichloroanilinoacetonitrile, 23.3 g of ethylenediamine p-toluenesulfonate and 75 milliliters (ml) of 1,2-dichlorobenzene was heated with stirring in a round-bottomed three-necked flask at from about 140°–170° C. for about 70 minutes under a small flow of nitrogen. The reaction mixture was cooled and then diluted with methylene chloride. The mixture was cooled and then filtered, which gave 35.1 g of 2-((2,4-dichloroanilino)-methyl)-2-imidazoline p-toluenesulfonate as white crystals. The p-toluenesulfonate salt was slurried in water and $CH_2Cl_2$ and then basified. The $CH_2Cl_2$ layer was separated and the remaining aqueous portion extracted with $CH_2Cl_2$ and then $CHCl_3$. The extracts were combined, treated with diatomaceous earth and activated charcoal, and then filtered. Concentrating the filtrate to dryness, left 17.0 g of crystals. Recrystallization from ethylene dichloride gave 14.0 g of purified 2-((2,4-dichloroanilino)methyl)-2-imidazoline as white crystals, having a melting point (m.p.) of 154°–156° C.

EXAMPLE 2

2-((2-Chloroanilino)methyl)-2-imidazoline Hydrochloride

The compound 2-((2-chloroanilino)methyl)-2-imidazoline p-toluenesulfonate was prepared using substantially the same procedure described above by heating a mixture of o-chloroanilinoacetonitrile (43.9 g), ethylenediamine p-toluenesulfonate (61.5 g) and 1,2-dichlorobenzene (198 ml). The p-toluenesulfonate salt was hydrolyzed to the free base, i.e., 2-((2-chloroanilino)methyl)-2-imidazoline by slurrying the p-toluenesulfonate salt in water, basifying the slurry and extracting the mixture with $CH_2Cl_2$. The methylene chloride was evaporated leaving 38.0 g of the free base. The free base was put in solution in isopropyl alcohol and acidified with hydrochloric acid in isopropyl alcohol which resulted in crystal formation.

Cooling the alcohol solution to 0° C. and filtering gave 41.7 g of crude product. Boiling methanol (~400 ml) was used to put the crude product in solution, and the solution was then treated with activated charcoal and filtered. The filtrate was cooled to −5° C. and filtered, which gave 34.6 g of 2-((2-chloroanilino)methyl)-2-imidazoline hydrochloride, m.p. 274°–275° C.

In practicing the method of the invention, the imidazoline compounds are brought into contact with sickle erythrocytes, typically by introducing an effective amount of the compound into the blood of a mammal having blood containing erythrocytes subject to sickling. Introducing an effective sickle inhibiting amount of the above-noted compound or pharmaceutically-acceptable salt into the blood of such a mammal can be carried out directly, e.g., by direct addition to blood samples, or indirectly, by administering the compound to the mammal in a manner effective to provide the sickle inhibiting concentration in the blood stream.

The compound or pharmaceutically-acceptable salt thereof would be introduced using a route of administration which provides an effective but non-toxic concentration of the compound in the blood, either by oral ingestion or direct administration as, for example, intravenous infusion or injection. The amount to be administered would vary depending on the compound or pharmaceutically-acceptable salt employed, the type of erythrocyte sickling inhibition or reversal desired, the size and nature of the mammal, and the manner of contacting the blood. When used to inhibit erythrocyte sickling in a mammal, the quantity of compound or pharmaceutically-acceptable salt to be administered in particular instances can be determined by routine procedures, such as studies of the concentration of the compound in the blood obtained at various time intervals after administration, using various methods of administration, and in vitro studies of the anti-sickling effect obtained with various concentrations of the compound in the particular blood in question.

The compounds described herein were tested in an "Oxygen-Affinity Assay" to measure the ability of the compound to influence the Hb-S oxygen affinity. There is a relationship between oxygen binding and Hb-S gelation and thus a measure of oxygen affinity is an index of Hb-S aggregation within the red blood cell. Hemoglobin S polymers decrease the overall oxygen affinity. Thus a return to normal of Hb-S oxygen affinity is a measure of decreased gelation.

For measurements of oxygen equilibria whole Hb-S blood was equilibrated in a tonometer at 37° C. and measurements were made in the presence of a 10 millimolar (mM) concentration of the test compound. The compound of Example 1 was also tested at a 5 mM concentration. The whole blood pH, oxygen tension, and blood $PO_2$ were measured. The percentage of oxygen saturation was plotted against the partial pressure of oxygen (mm Hg). The $P_{50}$ value (oxygen tension at 50% saturation) was determined for each control and treated whole blood sample and the difference ($\Delta P_{50}$) between the control and treated whole blood sample noted. As used herein, a negative $\Delta P_{50}$ represents a change toward a normal Hb-S oxygen affinity and thus is a measure of the test compound's ability to inhibit the sickling of sickle erythrocytes. The results of the Oxygen-Affinity Assays are presented in Table 1.

TABLE 1

| Compound Example Number | Oxygen-Affinity Assay $\Delta P_{50}$ | |
|---|---|---|
| | 10 mM | 5 mM |
| 1 | −10.2 | −10 |
| 2 | −5.5 | |

The data in Table 1 shows that the test compounds at a 10 mM concentration exhibited a negative $\Delta P_{50}$ which indicates that the test compound inhibited the sickling of sickle erythrocytes. The compound, 2-((2,4-dichloroanilino)methyl)-2-imidazoline also inhibited the sickling of sickle erythrocytes at a 5 mM concentration.

What is claimed is:

1. A method for inhibiting the sickling of red blood cells prone to sickle in blood containing said cells which comprises introducing into said blood an effective sickle inhibiting amount of a compound of the formula:

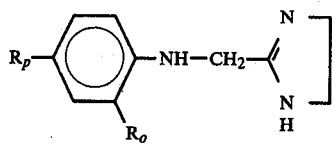

or a pharmaceutically-acceptable salt thereof, wherein $R_o$ represents chloro, bromo, fluoro or iodo; and $R_p$ represents hydrogen, chloro, bromo, fluoro or iodo.

2. The method of claim 1 wherein the compound is 2-((2,4-dichloroanilino)methyl)-2-imidazoline or a pharmaceutically-acceptable salt thereof.

3. The method of claim 1 wherein the compound is 2-((2-chloroanilino)methyl)-2-imidazoline or a pharmaceutically-acceptable salt thereof.

* * * * *